(12) United States Patent
Kriesel et al.

(10) Patent No.: US 10,807,767 B1
(45) Date of Patent: *Oct. 20, 2020

(54) STABILIZED STORAGE CONTAINERS

(71) Applicant: Tak Logic LLC, Ettrick, WI (US)

(72) Inventors: Matthew Wayne Kriesel, Melrose, WI (US); Troy Bradley Goodenough, Mindoro, WI (US)

(73) Assignee: Tak Logic, LLC, Ettrick, WI (US)

(*) Notice: Subject to any disclaimer, the term of this patent is extended or adjusted under 35 U.S.C. 154(b) by 953 days.

This patent is subject to a terminal disclaimer.

(21) Appl. No.: 14/999,722

(22) Filed: Jun. 20, 2016

Related U.S. Application Data

(60) Provisional application No. 62/231,004, filed on Jun. 22, 2015.

(51) Int. Cl.
| | | |
|---|---|---|
| *B65D 25/04* | (2006.01) |
| *A01K 97/06* | (2006.01) |
| *A61B 50/33* | (2016.01) |
| *B65D 33/06* | (2006.01) |
| *B05D 1/02* | (2006.01) |
| *C08G 18/48* | (2006.01) |
| *C08G 18/36* | (2006.01) |
| *C08G 18/10* | (2006.01) |
| *A61B 50/00* | (2016.01) |
| *A61B 50/30* | (2016.01) |

(52) U.S. Cl.
CPC .............. *B65D 25/04* (2013.01); *A01K 97/06* (2013.01); *A61B 50/33* (2016.02); *B05D 1/02* (2013.01); *B65D 33/06* (2013.01); *A61B 2050/002* (2016.02); *A61B 2050/3008* (2016.02); *C08G 18/10* (2013.01); *C08G 18/36* (2013.01); *C08G 18/4825* (2013.01); *C08G 18/4829* (2013.01)

(58) Field of Classification Search
CPC ........ B65D 25/04; B65D 33/06; A01K 97/06; A61B 50/33; A61B 2050/3008; A61B 2050/002; B05D 1/02; C08G 18/10; C08G 18/4829; C08G 18/36; C08G 18/4825
See application file for complete search history.

(56) References Cited

U.S. PATENT DOCUMENTS

| | | | | |
|---|---|---|---|---|
| 7,041,719 B2 * | 5/2006 | Kriesel | ..................... | A01L 7/02 524/114 |
| 2004/0134669 A1 * | 7/2004 | Kriesel | ..................... | A01L 7/02 168/14 |
| 2004/0191446 A1 * | 9/2004 | Kriesel | ..................... | A01L 7/02 428/35.7 |

* cited by examiner

*Primary Examiner* — Rabon A Sergent
(74) *Attorney, Agent, or Firm* — M. Paul Hendrickson; Bryan R. Rosiejka

(57) ABSTRACT

The invention provides a unique container combination comprised of a container equipped with a thermoset viscoelastomeric interfacing section which serves to confine items placed thereupon. The interfacing viscoelastomeric section may be chemically bonded to the container support or cohesively bonded thereto. The interfacing thermoset viscoelastomeric section adhesively immobilizes items placed thereupon while tenaciously clinging (chemically or adhesively) to the container supportive structure. Containers equipped with the thermoset viscoelastomeric section surprisingly create an aseptic environment especially adaptable to hygienic applications while also affording superior protection against impact damage.

21 Claims, 4 Drawing Sheets

STABILIZED STORAGE CONTAINERS

CROSS-REFERENCE TO RELATED APPLICATION

This application claims the benefit of U.S. Provisional Application No. 62/231,004 filed Jun. 22, 2015 and incorporates by reference herein the provisional application in its entirety.

FIELD OF INVENTION

The present invention relates to stabilized storage containers and the method of use thereof and more particular to stowing containers equipped with an interfacing section which maintains the placement of items.

BACKGROUND OF THE INVENTION

The age old problem of orderly maintaining items stored in container is well illustrated by the use of fishing tackle boxes filled with fishing equipment such as fishing lines, hooks, leaders, lures, etc. which upon opening after transport often reveals a snarled and entangled mess of fishing equipment. As a result, the fisherman often devotes precious fishing time to tediously untangle and prep the desired fishing equipment. The disarray of tackle box items sometimes leads to personal injury such as an inadvertent hooking injury.

It is practically impossible to maintain an orderly tackle box under its common environmental usage. Often the fishing tackle boxes are roughly handled or placed in a transport position which inherently causes the disarray. Boating to a fishing site also inherently creates conditions leading to a disarray of fishing tackle box contents. This may arise by wind and boating waves generated coupled with a speeding fisherman's boat inherently resulting in entangled fishing equipment. Numerous attempts to solve this age old problem have remained unsuccessful. The common practice of placing rubber mats in each of the individual tackle box compartments fails to correct the problem since the mats provide little, if any, cohesiveness to the tackle box or the stowed tackle.

The present invention solves this perplexing age old problem by the utilization of a unique thermoset elastomeric interfacing section adapted to be interfacially placed between the surfaces of the container and a stowed item. Items placed thereupon will remain in their original immobilized position notwithstanding substantial abusive, physical or environmental mishandling. Thus, for example, when the fisherman arrives at the fishing site everything within the tackle box remains as originally placed in at an appropriate position for instant use without delay.

BRIEF SUMMARY OF THE INVENTION

The present invention solves the age old problem of maintaining an orderly arrangement of stowed items in a container. The embodiments of the invention rely upon a stabilized combination comprised of a container equipped with a thermoset elastomeric interfacing section possessing unexpectedly superior adhesiveness to adhere to the container walls (including sidewalls, bed and top walls) while also tenaciously retaining and immobilizing any item emplaced upon the interfacing section. The interfacing section possesses unique adhesive and antipathogenic properties throughout its entire elastomeric structure. The interfacing sections may be conveniently provided as sheets (e.g. inlays or liners) or coatings applied to the walls including the bed and top walls of the stowing container. Since the thermoset elastomeric composition inherently possesses a highly tacky and adhesive character, the composition will remain adhesively bonded to the container as well as those items placed therein. The adhesion characteristics of the interfacing section, however, do not permanently adhere to objects which are placed in contact therewith but will adhesively disengage upon a withdrawing force without leaving any adhesive residue upon the application of a sufficient pulling force to disengage the stowed object from the thermoset elastomeric interfacing section. This enables a disengagement of the articles placed upon the interfacing section as well as from the container. To provide selective disengagement of the emplaced item from the interfacing section, physical alterations of the two interfacing section contacting surfaces (i.e. container and emplaced article contacting surfaces) may be utilized to permit a stronger adhesive attraction to the stowing container surface than the articles placed thereupon. This may be effectively accomplished by increasing the total contacting surface of the interfacing section which interfaces onto the stowing container while decreasing the overall contacting surface facing to the stowed object. Consequently lesser adhesive forces will exist at the item contacting surface than at the container interface. Alternatively the interfacing section may be chemically bonded to the container thus avoiding concern over the surface adhesion differences between the two surfaces.

DETAILED DESCRIPTION OF THE INVENTION

Figure 1:
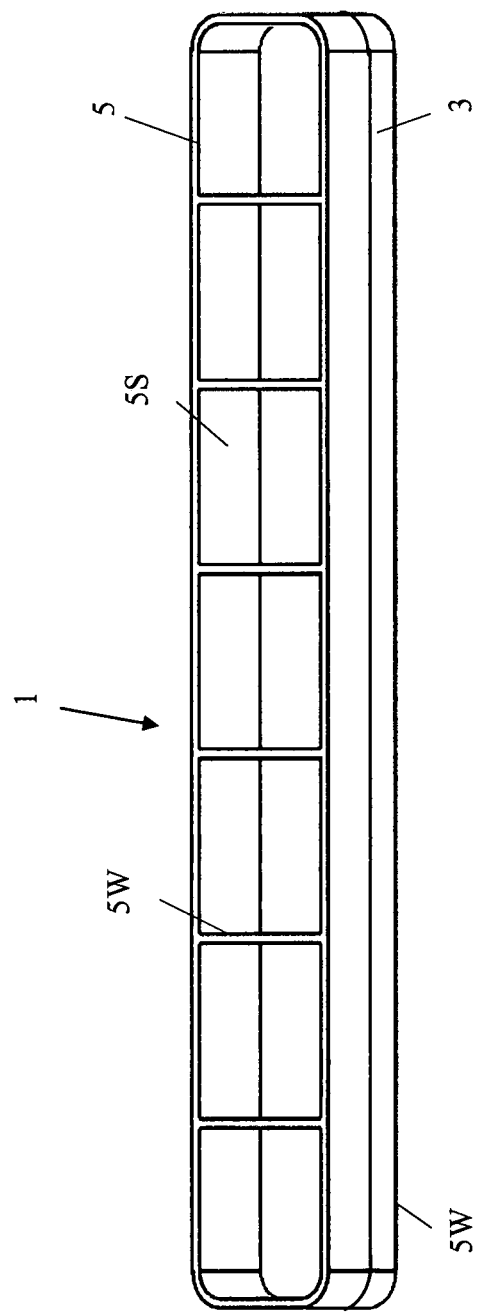
FIG. 1 is a perspective top view of a stabilized container combination comprised of a transparent container equipped with a thermoset viscoelastomeric interfacing section of this invention.

With reference to FIGS. 1-4, there is provided a stabilized stowing container combination 1 comprising a container 5 equipped with a stabilizing thermoset viscoelastomeric interfacing section 3 (often referred to as coating or liner) which stabilizes items 20 placed thereupon against unwanted displacement and movement. The containers 5 need only a supportive base or bed 5W since the exceptional adhesive properties of the thermoset viscoelastomeric overlay 3 serves to contain objects 20 placed thereupon. Crucial to the stabilizing effect is a unique thermoset elastomeric composition which imparts unique adhesive protection against impact force damage as well as antipathogenic properties to the container 5. Due to its fluid flow characteristics under stress and thermoset structure the thermoset polymeric composition is commonly referred to as a thermoset viscoelastomer. The cured viscoelastomeric composition provides a cured chemical formulation possessing a unique adhesive ability to cling onto objects or items 20 which come in contact therewith, but yet possesses an inherent property when properly fabricated to selectively release adhered objects or items 20 therefrom by applying an outwardly pulling force sufficient to overcome the tenacious adhesive forces of the thermoset elastomeric composition.

In the combination 1, the surface area of the viscoelastomeric section 3 will have a greater adhesive attraction to the container 5 than the objects 20 stowed thereupon. The embodiments of the stabilized stowing container combinations 1 are respectively illustrated transparently in FIG. 3 as a fishing tackle container (generally prefixed by 5) and a pill box container 5 equipped with compartmentalized sections 5S having a thermoset elastomeric interfacing section 3 (e.g. an overlaying 3 such as a liner 3 or chemically bonded coating 3) adherently affixed to the interfacial surfaces of the container 5 (including its bed wall) so as to contain items or objects 20 which may be placed thereupon. Due to its unique and superior adhesiveness the thermoset viscoelastomeric interfacing section 3 may be provided in a form which provides sufficient interfacial surface contact so as adhere (physically or chemically) to the container walls 5W (including sidewalls, top walls and bed walls of the container 5) while also providing a sufficient interfacial adherence to any item 20 so as to retard or immobilize movement of the item 20 placed thereupon. The interfacial adherence of the thermoset elastomeric section 3 to the container walls 5W may be effectuated by any container manufacture which supplies a sufficient quantum of the thermoset viscoelastomeric section 3 to immobilize items 20 desired to be stowed by the stabilized container combination 1. The thermoset elastomeric composition of the interfacing section 3 is manufactured under thermosetting conditions in which the thermosetting precursor reactants immersed in a lipophilic reactant as the predominate media component are cured in the presence of curing under thermosetting reaction conditions so as to create the desired thermoset elastomeric manufacture for adhesive insertion onto the container 5. Alternatively, the thermoset viscoelastomeric composition may be applied (e.g. spray coating, injection molding, casting, etc.) as an uncured or thermosetting reactants to the container walls 5W or container compartments 5S and allowed to cure in situ to provide a thermoset elastomeric coated section or coating 3 chemically bonded to the container 5. By applying the uncured reactants to the desired container wall 5W sections, the uncured thermoset viscoelastomeric coating 3 when cured becomes chemically bonded to the container surface to provide a permanent bonding thereto.

The uncured thermosetting reactants may accordingly be directly deposited (e.g. sprayed, injected, casted etc.) onto the container walls 5W and allowed to cure into the desired thermoset elastomeric interfacing section or coating 3. Thus, the uncured thermosetting reactants may be applied as coatings, strips, systematic castings (e.g. circles, spirals, etc.) or in any other fabricating form sufficient to create a thermoset viscoelastomeric interfacing section 3 of a sufficient size to hold or immobilize the intended items 20 for placement thereupon. Injection molding, spray coating, vacuum molding, blading, spreading and other coating techniques may be used to apply the uncured reactants to the container walls 5W (i.e. top walls, sidewalls and/or bed wall). The curing rate and flow characteristics (viscosity) of the uncured reactants can be effectively controlled by the type and amount of catalytic agents, reactants, thermal conditions, etc. The reactants may also prefabricated as insertable liners 3 by calendaring, sheeting, etc. manufacture of the uncured reactants which upon curing may cut to fit the compartmentalized container sections 5S.

Figure 2:
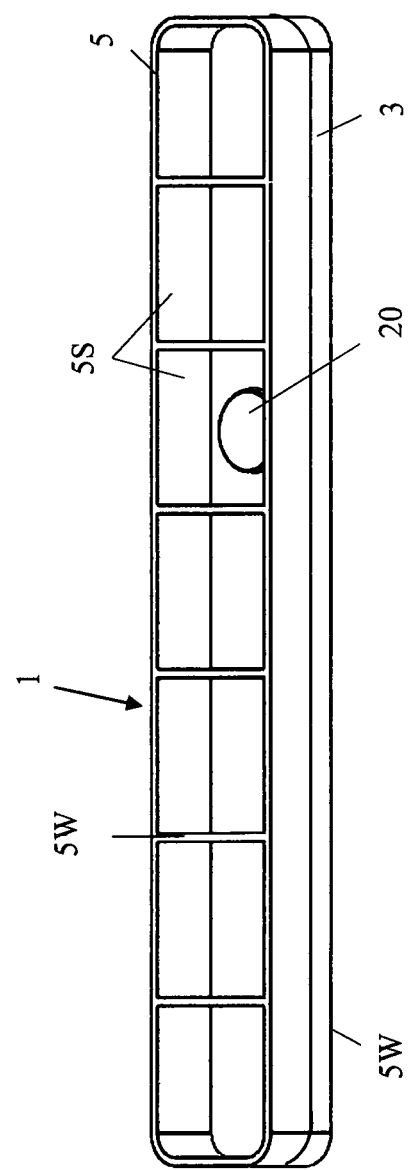
FIG. 2 is a perspective top view of the transparent pill box combination shown in FIG. 1 in which one of the pill compartments contains a medicinal pill.
Figure 3:
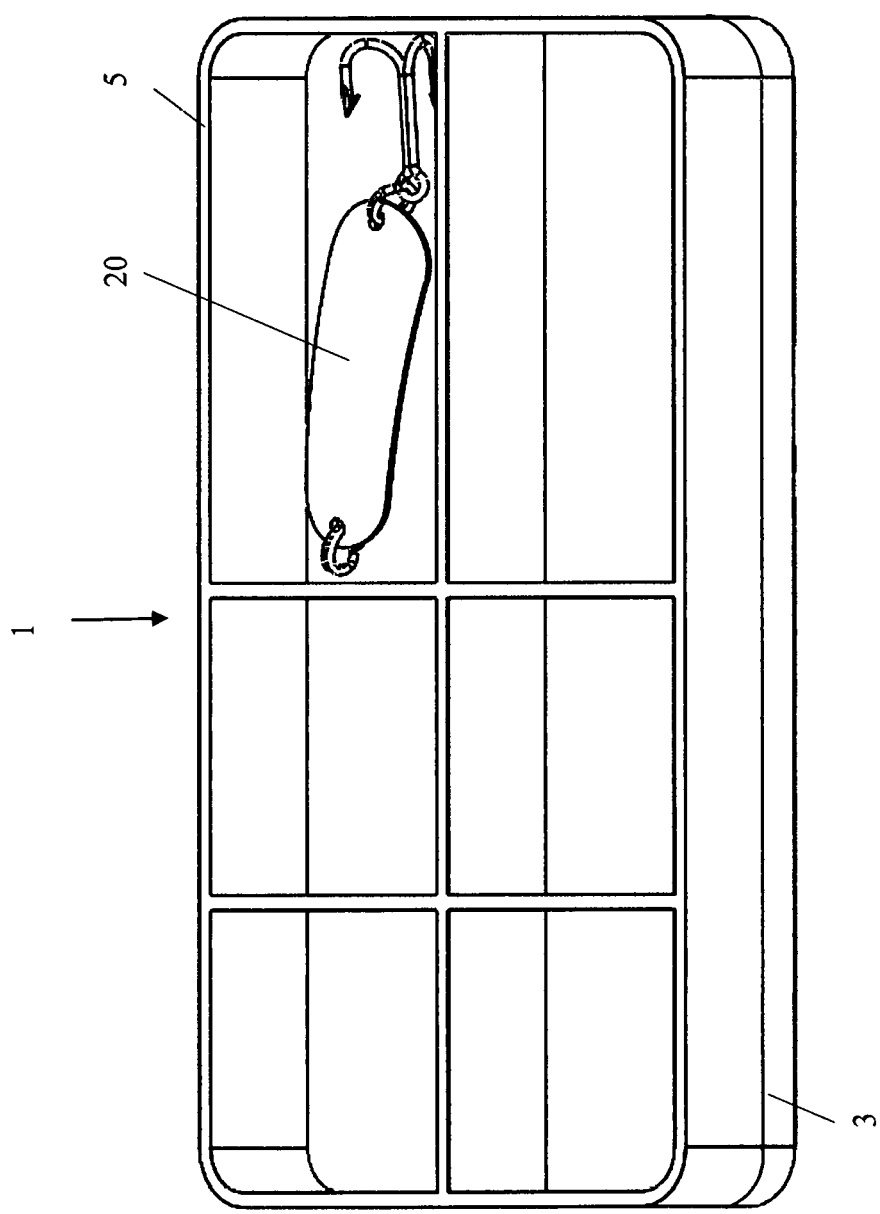
FIG. 3 is a partial perspective view of a stabilizing container combination of this invention having a fishing lure placed therewithin.

The fishing tackle and medicinal pill boxes 5 of a transparent construction shown in FIGS. 2-3 embody several embodiments of the invention. In the FIGS. 2-3 depiction, the layered sheet like construction of the interfacing thermoset elastomeric section 3 resting upon the bed 5W of the compartmentalized container units 5S of the pill box container 5 are clearly visible. When the interfacing thermoset elastomeric section 3 comprises an insertable liner 3, the adhesive character of the respective surfaces can be altered so as to selectively release the item 20 while maintaining adherence to the bed wall 5W of the container 5. Such changes may be implemented by providing a bottom surface which adheres to the bed 5W of the container 5 as a substantially flat or smooth surface whereas the upper surface may be an irregular surface containing pronounced ridges and valleys to substantially reduce its surface contact area with the item 20 and its concomitant adhesiveness.

The interfacing section 3 as used herein differs from conventional thermoplastic strips and rubbers, etc. which normally require an adhesive adjunct to adhere to an object 20. Unlike such conventional thermoplastic strips, the thermoset viscoelastomeric section 3 used herein possesses sufficient adhesive properties throughout its entire compositional structure to adhere to most thermosets and thermoplastics container wall beds 5W. The thermoset viscoelastomeric reactant provide excellent bonding precursors for bonding to the container 5. The permanently inherent adhesive properties are tenaciously bound within its compositional make-up making it virtually impossible to leave any adhesive compositional residue when the elastomeric section 3 separates from a container 5 or upon a removal of an item 20 emplaced thereupon.

There exist special benefits for certain container uses by providing the thermoset polymeric interfacing section 3 in a removable liner form so as to permit periodic removal of the section 3 from the container walls 5W. The interfacing section 3 may be tailored so as to fit the container 5 or its compartmentalized sections 5S. This constitutes an advantage for certain type of containers 5 and especially for small compartment sized containers 5. Since the thermoset polymeric interfacing section 3 is prone to adhere to a host of objects 20 which come into contact therewith, the thermoset polymeric interfacing section 3 is also prone to accumulate dust, dirt, linen, and other contacting contaminates exposed to its surface. Excessive accumulations of such contaminates can dramatically reduce the adhesive characteristics of the thermoset elastomeric interfacing section 3 to the extent it may no longer possesses a sufficient capacity to stabilize and immobilize objects 20 placed upon its interfacing surface. The accumulation of unwanted foreign matter upon the thermoset elastomeric interfacing section 3 surface may be effectively removed by washing with common soaps and water which restores its adhesive efficacy. By providing a thermoset elastomeric interfacing section 3 in a removable form (e.g. castings, sheet, etc. form), any foreign matter clogging its adhesive surface may accordingly be readily removed and restored to effective use by washing. Thus, by providing the thermoset viscoelastomeric interfacing section 3 in a removable form provides certain advantages.

Although the providing of the viscoelastomeric section 3 as an insertable and removable liner 3 for ease of cleaning, the uncured viscoelastomeric reactants when cured in situ with a restraining container or receptacle 5 will result in a tenacious and permanent chemical bonding therebetween. For many container combinations 1, the chemically bonded form is most desirable. In certain applications in which the container 5 affords a sufficient flat open surface area to permit the surface to easily be washed and cleansed from air borne and other contaminants, the chemical bonding provides superior benefits.

Figure 4:
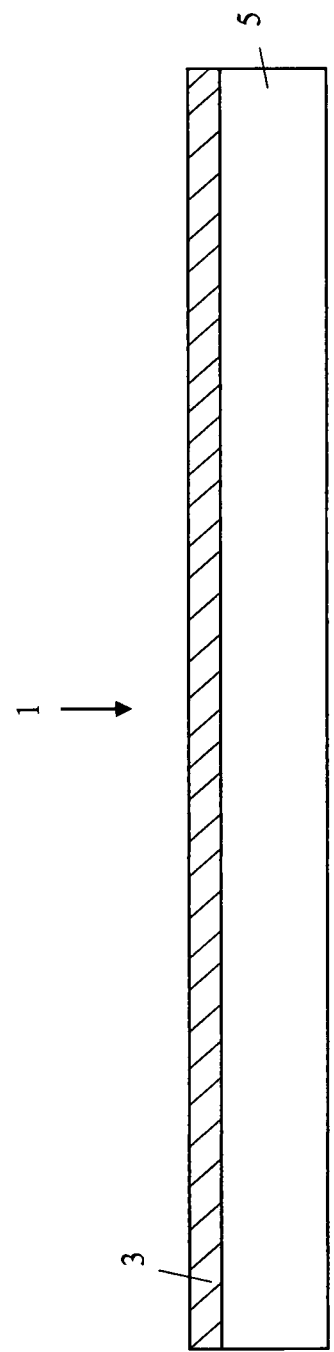
FIG. 4 is an illustrative cross-sectional view of a tray coated with the thermoset viscoelastomeric coating.

For certain applications, the thermoset viscoelastomeric section 3 in combination with a flat surfaced container such as in a tray creates a confining container 5 for the combination 1 without the need of sidewalls as illustrated by the tray of FIG. 4. The thermoset viscoelastomeric section 3 bonded to the supportive bed wall 5W of the container 5 serves to confine an item 20 placed thereupon and supported by the confining container 5. Due to the cohesiveness of the overlaying viscoelastomeric section 3, the need for a raised edge or rim for a flat surfaced container 5 such as trays may be accordingly eliminated. This is particularly useful for application within hygienic field such as the common usage of dental and medical trays at medical and dental clinics, hospitals, examining rooms, etc. Due to the unique properties of the thermoset viscoelastomeric section 3 properties, the ability to hold in place medical and dental instruments in a sterile environment represents a significant advance over the current state of the art. The permancy of the chemical bonding between the container or receptacle 5 and the bonded tacky viscoelastomeric coating 3 further provides an advantage over the existing state of the art. It is therefore evident that for certain end uses the removable liner or section 3 (e.g. highly compartmentalized small open surface areas) is best suited whereas the chemically bonded form for the access friendly type of confining containers 5 chemically bonded serves best.

Casted, layered, filmed, sheeted etc. forms of the cured interfacing section 3 may be prepared by initially depositing the uncured thermosetting elastomeric reactants in a suitable form (e.g. compartmentalized sections 5S, etc.), such as by casting, injection molding, calendaring, or by depositing measured amounts of the uncured reactants upon a moving belt (equipped with or without heating) etc. and thereafter allowing the uncured reactants to spread to the desired interfacing section 3 thickness. Upon curing in a calendared, strip, sheet, casted, etc. form, the cured mass of the interfacing section 3 may then be cut or sized to match the compartmentalized wall sections 5W of its intended end use. Similarly the appropriate uncured reactant dosage needed to provide the desired configuration and coating thickness of the thermoset elastomeric section 3 may be directly applied to the container walls 5W which upon curing will create the desired stabilized container combination 1. In the uncured form, the thermoset reaction media can be formulated so as to provide the desired flow characteristics to permit the casting of an interfacing coated section 3 of a desired configuration and thickness.

The present invention may be broadly adapted to a broad range container combinations 1. Items 20 weighing a gram or less to those weighing a pound or more may be effectively stabilized and confined to their original container placement position. The degree of immobilization exerted upon any item 20 placed upon the interfacing section 3 will have a direct bearing upon the total contacting surface area of the interfacing section 3. A greater interfacial surface contact area leads to a greater adhesion to items 20 so as to allow a placement for heavier items 20.

As illustrated by FIG. 2, compartmentalized pill boxes 5 for stowing medicinal pills may effectively benefit from use of the thermoset elastomeric interfacing section 3 herein. The elastomeric section 3 may be chemically bonded to container bed 5W or as a removable bed liner 5W. Similarly stowed items 20 larger or weighing more than fishing tackle equipment such as carpentry or mechanical tools as commonly stowed in tool boxes can also benefit from the container combination 1 and the stabilization features of this invention. The stowing container combination 1 need not be of a rigid structure. Flexible stowing container combinations 1 such as flexible medical equipment containers, flexible photographic equipment containers, tool bags, fishing tackle bags etc. of a fabric construction and other types of flexible container 5 may effectively achieve the unique benefits of this invention. Since the thermoset elastomeric section 3 adhesively adheres to items 20 placed thereupon, the container combination does not necessitate traditional sidewalls or covering lids.

In another embodiment of the invention as illustrated by FIGS. 2-4, the thermoset polymeric interfacing section 3 may be utilized to impart a desired sanitizing effect to the stowing container combination 1. The interfacing section 3 inherently imparts anti-microbial and anti-fungal properties to the container combination 1. Thus, when the interfacing elastomeric section 3 (e.g. coating, siding. sheathing, film, layer, etc.) is applied to a wall or bed 5W of a container 5, the exposed outer and inner container surfaces of the interfacing section 3 inherently imparts anti-pathogenic properties to the container combination 1. The thermoset polymeric interfacing section 3 accordingly does not foster, but rather prevents the development of unhealthful pathogenic, microbial or fungal infestation. Thus, the use of the thermoset polymeric interfacing section 3 for surgical and medical as well as other hygienic uses along with its inherent self-adhesive and shock absorbing characteristics uniquely distinguishes its unexpected efficacy from other adhesive polymeric materials and conventional compartmentalized containers. Accordingly, medical and other hygienist containers 5 for retaining hygienic items 20 such as medical or hygienist cabinet compartments, bags, kits, boxes including pill boxes, surgical, examining, medical and dental trays, etc. supportive and interfacing onto the thermoset elastomeric section 3 afford unexpectedly superior advantages over the current technology of maintaining an orderly, sterile and systematic placement of medical instruments, devices and compositions in a stabilized adherent and sterile environment, all of which benefits fulfill a long sought medical and hygienist need. Should dust and other debris including air borne particles contaminate or clog the adhesive surface of the thermoset elastomeric interfacing section 3, it may be readily restored to its original adhesive condition by a soap and water wash without adversely affecting its antibacterial and fungal properties which uniformly permeate throughout its entire compositional structure.

Thus, the thermoset elastomeric interfacing section 3 is particularly well suited for hygienist use. Medical and dental and hygienist related containers 5 such as used by First Responders, ambulance personnel, dentists, dental hygienist, physicians, surgeons, nurses, etc. are beneficially bestowed with a unique stabilizing container combination 1 for stowing self-contained items 20 in a stabilized, immobilized, sterile and orderly environment. The term "interfacing section 3" herein refers to any interfacial physical adhesive contact or a chemical bonding between the thermoset viscoelastomeric section 3 to any supportive structure 5 capable of confining the stored item 20 via the adhesive viscoelastomeric section 3. The interfacing section 3 may be in the form of a coating (continuous or discontinuous) sheathing, siding, film, slab, sheet, casting and the like comprised of the thermoset elastomeric interfacing section 3 which forms an interface with the confining container (e.g. beds, walls 5W, etc.). As previously mentioned the interfacing intersection may permanently bond (e.g. in situ curing)

or as a removable liner 3. Since the adhesiveness of the thermoset viscoelastomeric section 3 serves to confine an adherent item 20 placed thereupon, the container 5 can avoid the need for compartmentalized containers as is the case for tray containers 5 coated with the object 20 containing coating 3.

The uncured thermoset viscoelastomeric reactants may be colored to suit any desired coloring or coding for the interfacing section 3 and the end use of the combination 1. If desired, the uncured reactants may be formulated so as to provide a transparent interfacing section 3 which permits locating indicia, labels, decals, written messages such as item use instructions, etc. to be clearly visible through the transparent interfacing section 3. Coloring additives such a pigments, dyes, etc. may also be formulated into the uncured reaction media to provide desired coloring effect. The interfacing section 3 may similarly be color coded to identify the stowed items 20 immobilized within the confinement of the container 5. Similarly fragrances may also be formulated into the uncured reactants to provide a scented interfacing section 3. If desired, the interfacing section 3 may also be externally utilized to retain stacked or otherwise arranged containers 5 in an orderly fashion. If desired, identifying coded coloring indicia being used to identify the respective contents of each container 5 of the combination 1.

The interfacing section 3 has a broad range of adhesive affinity to containers 5 as well as most items 20 placed thereupon which embraces of a wide range of diverse construction of materials. The interfacing section 3 may be used to physically adhere or chemically bond a host of solid or supportive substances. Thus, container 5 and the objects 20 confined by the thermoset viscoelastomeric section 3 may be illustratively constructed of a wide range of diverse materials such as cellulosic materials (e.g. wood, wood composites, vegetative materials, etc.), thermoset plastics, thermoplastics, plastic composites, metals (e.g. aluminum, steel, tin, metal alloys, etc.), glass and a host of other solid supportive materials. Thus, the combination 1 broadly applies to any supportive substance compatible with the interfacing section 3. Certain of the halogen containing polymers (e.g. PVC) are neither physically cohesively nor chemically compatible with the adhesive properties of thermoset viscoelastomeric section 3.

The interfacing section 3 is non-toxic, environmentally green friendly, virtually free from residual gases and volatizing of any residual gases. The interfacing section 3 also possesses superior impact and vibration absorbing attributes which further serves to protect stowed objects 20 from impact and vibrational damage. Accordingly fragile emplaced items 20 such as a photographic lens, glass syringes and containers, fragile electronic equipment, circuit boards and other delicate items 20 etc. may be protectively housed and/or restrainingly immobilized against damage and injury.

The thermoset viscoelastomeric interfacing sections 3 as used in the combination 1 herein are typically less than 4 mm in thickness with the removable liner more typically having a thickness of less than 3 mm. In the coated and chemically bonded form a substantially lesser amount of the viscoelastomeric section 3 will effectively provide and adhesive surface. Typically a coated section 3 will be less than about 60 mil thickness and most typically within a thickness range ranging from about 20 mil to about 50 mil.

U.S. Pat. No. 7,041,719 B2 to Matt Kriesel and Troy Goodenough generally discloses as background technology a group of polyurethanes (thermoset) colloidal polymerizates which when properly formulated can be utilized for preparing the interfacing section 3. The formulation of the uncured reactants needs to be formulated so as to impart the desired adhesive characteristics of the cured reactants. This generally entails decreasing the oil reactants to less than 50 percent of the reactants weight (but still as the predominate reactant reaction media ingredient) while increasing the backbone chain of polymerizable reactants. The general technology taught by U.S. Pat. No. 7,041,719 encompasses a broad range of thermoset elastomeric compositions capable of producing a host of polymeric compositions possessing surprisingly unique polymeric properties. Although the primary thrust of the teachings rests upon formulations exhibiting uniquely superior impact absorption properties possessing a slight or moderate tacky touch which are generally insufficient to effectively immobilize items 20 placed upon its surface. Surprisingly the polymeric tack characteristics of the thermoset elastomeric composition may be made to possess a higher degree of tack by making formulation changes which alter its compositional make-up and properties. Surprisingly by reducing the triglyceride oil (e.g. epoxidized) content and increasing the proportion of certain other thermoset polymerizable reactants, the cured tackiness of the interfacing section 3 will dramatically increase although the reaction media will still contain a triglyceride component (e.g. epoxidized soybean oil) as the predominate component. In general, the more highly cross-linked thermoset colloidal compositions as typically disclosed by U.S. Pat. No. 7,041,719 B2 lack the desired high degree of tack for effective use herein. Increasing the compositional adhesiveness generally entails decreasing the epoxidized oil content and decreasing the triol reactant so as to reduce cross-linkage while also increasing the diol reactant level to enhance linear polymeric formation within its thermoset structure. Superior tack efficacy is achieved when the triglyceride content ranges from about 40 to less than 50 percent by weight of the total reaction media weight.

Traditionally polyurethanes are formed by reacting a polyol with a di- or polyisocyanates such as the aromatic isocyanates (e.g. typically a diphenylmethane diisocyanate-MDI or tolune diisocyanate-TDI) and aliphatic isocyanates such as hexamethylene diisocyanate (HDI) or isophorone diisocyanate (IPDI) as the polyurethane isocyanate reactant. Particularly effective reactant components for providing the interfacing section 3 are certain prepolymers of an isocyanate reacted with polyoxy akylene diols prepolymers such as the polyoxyethylene and/or polyoxypropylene diols having a 1000 to about 2000 molecular weight.

The interfacing section 3 as depicted FIGS. 1-4 may be appropriately prepared using the thermosetting precursor reactants to provide a carbamate linkage (e.g. urethane) of the thermoset polyurethane polymerizate. In general, the applicable thermosetting polyurethane precursor mixes for preparing the interfacing section 3 include a plasticizing amount of a polyol prepolymers reacted with a ring-opening species of a hardener (e.g. amines, amides, mercaptans, anhydrides, polycyanates such as a diisocyanate, etc.). The di or polyol reactants, hardeners, catalyst, reaction temperatures, etc. are appropriately pre-selected so as to provide the desired interfacing section 3. The use of reactants, catalysts, reaction temperatures, etc. which lead to excessively stiff cross-linked thermoset polymers are generally unsuitable. Such undesirable thermoset polymerizates typically exhibit both a high degree of cross-linkage and glass transition temperature. Reaction conditions and reactants which yield a more flexible plasticized thermoset polymeric backbone structure are particularly applicable for use herein. Since the highly exothermic and elevated curing temperatures are more conductive to the more rigid thermosets; the reactants, slower reaction rate catalysts, low curing temperatures and prolonged curing times will most appropriately impart the desire interfacing section 3 characteristics. These conditions also generally create a more flexible, lower degree of cross-linkage and a lower glass transition temperature. The thermoset interfacing section 3 is compositionally characterized as being a viscoelastomeric thermoset polymers exhibiting low rebound velocity and hysteresis properties. Such viscoelastic thermoset polymers also characteristically exhibit excellent energy and attenuating properties capable of withstanding repetitive and prolonged stock stress without structural damage or any substantive sag or rebound loss.

The viscoelastomeric thermoset polymers as disclosed in the Kriesel et al. '719 patent set forth the basic thermoset polymeric preparatory steps which may also be applied to the interfacing sections 3 herein. Procedurally this involves reacting a formulated mix of an epoxidized vegetable oil as a predominant weight reactant (typically more than about 40% of the total reactant mixture weight), a polyhydric material having a molecular weight of more than 1,000 and an isocyanate prepolymer (e.g. aliphatic, aromatic, heterocyclic, etc. polyisocyanates, cycloaliphatic, arylaliphatic) along with an appropriate catalyst (e.g. slow acting catalyst) which provides a desired thermosetting reaction rate and significantly assists in providing a formulated curable thermosetting precursor mix for a controlled fabrication of the interfacing section 3. Illustrative catalysts include the tertiary amines the tertiary phosphines, strong bases (e.g. alkali and alkaline earth metal hydroxides, alkoxides and phenoxides, and the acidic metal salts of strong acids, metal chelates, metal alcholates and phenolates, organic acid salts, organo metallic derivatives etc. (e.g. see column 4 line 35-column 5, line 32 of U.S. Pat. No. 7,041,719).

The di- and polyols of a relatively high molecular weight also effectively serve as the plasticizing polymeric reactants. On a reactant weight basis percentage basis, the diols are generally less effective as a plasticizer than the triols, but most effective as an adhesive contributor. The triols typically require a lesser amount of reactant while also generally contributing to a more highly branched plasticized linkage within the thermoset polymeric structure. To achieve the desired plasticizing effect, the diols are usually of a relatively high molecular weight. In general, the plasticity and flexibility may be effectively imparted via interpolymerizing the higher molecular weight diols or polyols (e.g. molecular weight 2,000-10,000) with other thermosetting reactants. The diols are typically comprised of a straight chain molecule having two terminal hydroxyl groups while the triols have three terminal hydroxyl groups.

The epoxidized vegetable oils contribute towards providing the desired cured flexibility, plastization and adhesion efficacy of the cured thermoset. Particularly effective cohesive properties arise when the epoxidized vegetable oil content ranges between about 35 to less than 50 parts by weight of the total reaction media weight. The epoxidized vegetable oil will most effectively comprise a predominate weight portion of the total reactant media, typically in an amount ranging from about 40 to less than 48 percent by weight of the total reactant weight. The molecular size and configuration, polarity, functional molecular groups etc. of the epoxidized vegetable oil accordingly contribute to the creation of the desired cohesive interfacing section 3. Although the epoxidized vegetable oil may include a variety of epoxidized vegetable oils (e.g. castor, corn, cotton seed, perilla, safflower, linseed, soybean, tall, etc.), epoxidized soybean oil is especially effective as the epoxidized vegetable oil component for preparing the cohesive interfacing section 3.

Imparting the desired flexibility and adhesive characteristics compatible for interfacing onto the container confining walls 5W including the container bed 5W and items 20 confined thereby may be illustratively effectuated via utilizing a polyurethane precursor mix containing about 10 to about 20 percent by weight (e.g. ELASTOCAST C-4057 a two functional polyether polyol), about 25 to about 35 percent by weight of a three functional polyether polyol (e.g. ELASTOCAST C-4018 by BASF), about 4 to about 7 percent by weight of methylene diphenyl diisocyanate based polyether prepolymer (e.g. ELASTOCAST TQZ-P23 by BASF Corporation), about 42 to less than 50 percent by weight of an epoxidized soybean oil and a catalytic amount of suitable catalytic (e.g. and a Bismuth (3+) neodecanoate-COSCAT 83 supplied by Vertellus Specialties) typically at a catalytic concentration ranging from about 0.1 to about 0.6 percent by weight of the total reactant weight. Exemplary of other diisocyanate reactants includes prepolymers of methylene diphenyl diisocyanate reacted with polyoxyethylene polyoxypropylene diols with a molecular weight ranging from 1000 and 2000 such as sold under Isonate 2181® and Rubinate 1790® trademarks.

As a reaction media component, the epoxidized vegetable oils are particularly effective compositionally in producing the desired thermoset polymeric colloidal for the interfacing section 3. The epoxidized triglycerides of the vegetable oil have been observed to uniquely contribute towards the desired prerequisite viscoelastic properties while also imparting the desired cohesive attributes adaptable for use in combination with the confining container 5 and the items 20 desirably immobilized by the interfacing section 3.

As may be observed from the aforementioned formulation, the epoxidized vegetable oil most suitably constitutes the predominate ingredient of the uncured reaction media. Initially the uncured reactants are formulated so as to possess sufficient flow characteristics which allows the uncured reactants to be performed into a desirable shape for use as the interfacing section 3 herein. By regulating the reactants and curing conditions (inclusive of the catalyst and inhibitors) the rate at which the reactants cure to the desired degree of thermoset and colloidal dispersion may be effectuated.

In general, the cured thermoset elastomeric composition prepared from uncured reactants do not permanently adhere to most forming or molding forms except for certain type of adhesive compatible materials such as the polyurethanes and PET (e.g. polyethylene terephthalate) polymers while other materials such as polyvinylchloride (PVC) possess excellent release properties which renders them effective for use as a mold to cure the reactants. The medical antipathogenic or aseptic properties of the interfacing section 3 render it highly effective for medical and hygienic uses. Surgical trays, examining room trays, dental and dental hygienist trays, etc. having the interfacing section 3 possess the surprising ability to immobilize surgical, medical and dental instruments placed thereupon while also providing a surprising aseptic and sterile environment.

Container Combination 1
Thermoset viscoelastomeric interfacing section 3
Supportive container walls 5W
Compartmentalized container sections 5S
Items 20
Container 5

What is claimed is:

1. A storage container combination possessing sufficient adhesiveness to adhesively engage and contain an item placed thereupon, wherein the storage container combination comprises:
   A. a container having sufficient supportive structure to support an item placed thereupon; and
   B. a thermoset viscoelastomeric interfacing section positioned in an interfacing relationship to the supportive structure with said thermoset viscoelastomeric interfacing section comprising a thermoset reaction product of a thermosetting reaction media comprising about 10 to about 20 percent by weight polyether diol, about 25 to about 35 percent by weight polyether triol, about 4 to about 7 percent by weight of an diisocyanate based prepolymer, about 35 to less than 50 percent by weight of an epoxidized vegetable oil and a catalytic amount of a curing catalyst therefore.

2. The storage container combination according to claim 1 wherein the epoxidized vegetable oil comprises an epoxidized soybean oil in an amount ranging from about 42 to about 48 percent by weight of the total reaction media weight.

3. The storage container combination according to claim 2 wherein the container comprises a multiple compartmentalized container having at least one compartment interfacing onto the thermoset viscoelastomeric interfacing section.

4. The storage container combination according to claim 3 wherein the container comprises a rigid container equipped with multiple container beds interfacially contacting onto the thermoset viscoelastomeric interfacing section.

5. The storage container combination according to claim 4 wherein the container comprises a fishing tackle box.

6. The storage container combination according to claim 5 wherein the combination further includes fishing tackle immobilized within the fishing tackle box by said thermoset viscoelastomeric interfacing section.

7. The storage container combination according to claim 6 wherein the fishing tackle includes multiple fishing lures.

8. The storage container combination according to claim 3 wherein the container comprises a flexible container.

9. The storage container combination according to claim 8 wherein the container comprises a bag with handles.

10. The storage container combination according to claim 1 wherein the container comprises a hygienic container equipped with the thermoset viscoelastomeric interfacing section comprising sufficient hygienic properties to substantially inhibit pathogenic growth thereupon, and further comprising sufficient surface adhesiveness to immobilize a hygienic item placed upon the thermoset viscoelastomeric interfacing section.

11. The storage container combination according to claim 10 wherein the container comprises a tray for storing medical or dental instruments.

12. The storage container combination according to claim 3 wherein the thermoset viscoelastomeric interfacing section is prepared from an uncured reaction media.

13. The storage container combination according to claim 12 wherein the thermoset viscoelastomeric interfacing section is chemically bonded to a surface area of the container by curing the reaction media in situ upon the surface area.

14. The storage container combination according to claim 13 wherein the container is a hygienic container possessing antipathogenic properties imparted thereto by the thermoset viscoelastomeric interfacing section.

15. The storage container combination according to claim 13 wherein the polyether diol consists essentially of a polyoxyethylene diol and a polyoxypropylene diol, each having a molecular weight ranging from about 1000 to about 2000.

16. A method for preparing a container combination comprising an aseptic surface and sufficient adhesiveness to retain a stored item placed thereupon, said method comprising:
   A. providing a container having a surface area of a sufficient structural support to support the item placed thereupon;
   B. placing a thermoset viscoelastomeric section in an interfacing relationship to the surface area with the thermoset viscoelastomeric section comprising a thermoset of a thermoset viscoelastomeric reaction media comprised of:
      a) about 10 to about 20 percent by weight polyether diol;
      b) about 25 to about 35 percent by weight polyether triol;
      c) about 4 to about 7 percent by weight di-isocyanate based prepolymer; and
      d) about 42 to less than 50 percent by weight of an epoxidized vegetable oil; and
   C. reacting the thermoset viscoelastomeric reaction media in the presence of a catalytic amount of a thermosetting catalyst.

17. The method according to claim 16 wherein the method includes initially coating the surface area with the thermoset viscoelastomeric reaction media and thereafter allowing the thermoset viscoelastomeric reaction media to thermoset.

18. The method according to claim 16 wherein the container combination comprises a rigid container having multiple compartments equipped with the thermoset viscoelastomeric interfacing section.

19. The method according to claim 18 wherein the container comprises a fishing tackle box.

20. The method according to claim 17 wherein the combination comprises a hygienic container.

21. The method according to claim 20 wherein the reacting includes a chemical bonding of the thermoset viscoelastomeric reaction media onto the surface area of the hygienic container by an in situ curing of the thermoset viscoelastomeric reaction media applied to the surface area to provide a chemically bonded interface.

\* \* \* \* \*